United States Patent
Banasiak et al.

(10) Patent No.: US 11,426,332 B2
(45) Date of Patent: Aug. 30, 2022

(54) SHADE-COORDINATED, VENEERING PORCELAIN SYSTEM FOR DENTAL PROSTHESES

(71) Applicant: DENTSPLY SIRONA Inc., York, PA (US)

(72) Inventors: Slawomir Banasiak, Kearny, NJ (US); Vicky Nemzer, Newtown, PA (US); Christopher Chu, West Windsor, NJ (US); Dan Ammon, York, PA (US)

(73) Assignee: DENTSPLY SIRONA INC., York, PA (US)

( * ) Notice: Subject to any disclaimer, the term of this patent is extended or adjusted under 35 U.S.C. 154(b) by 824 days.

(21) Appl. No.: 15/729,208

(22) Filed: Oct. 10, 2017

(65) Prior Publication Data

US 2018/0098918 A1 Apr. 12, 2018

Related U.S. Application Data

(60) Provisional application No. 62/406,190, filed on Oct. 10, 2016.

(51) Int. Cl.
| | | |
|---|---|---|
| *A61K 6/802* | (2020.01) | |
| *A61K 6/20* | (2020.01) | |
| *A61K 6/818* | (2020.01) | |
| *A61K 6/833* | (2020.01) | |
| *A61C 13/08* | (2006.01) | |
| *A61C 13/083* | (2006.01) | |

(52) U.S. Cl.
CPC ............ *A61K 6/802* (2020.01); *A61C 13/082* (2013.01); *A61C 13/083* (2013.01); *A61K 6/20* (2020.01); *A61K 6/818* (2020.01); *A61K 6/833* (2020.01)

(58) Field of Classification Search
CPC .... B32B 1/00; B32B 7/00; B32B 7/02; B32B 7/022; B32B 7/027; B32B 9/00; B32B 9/005; B32B 9/04; B32B 18/00; Y10T 428/24942; Y10T 428/24983; Y10T 428/24992; A61C 13/00; A61C 13/08; A61C 13/083; A61C 13/09; A61C 2201/00; A61C 2201/002; A61K 6/00; A61K 6/15; A61K 6/20; A61K 6/80; A61K 6/802; A61K 6/849; A61K 6/853; A61K 6/871; A61K 6/876; A61K 6/878; C03C 3/00; C03C 3/04; C03C 3/076; C03C 3/078; C03C 3/083; C03C 3/085; C03C 3/087; C03C 4/00; C03C 4/0007; C03C 4/0021; C03C 10/00; C03C 10/0009; C03C 10/0018; C03C 10/0027; C03C 10/0036

USPC ....... 428/688, 689, 697, 699–702, 212, 217, 428/218; 106/35; 433/167; 501/11, 27, 501/31, 53, 55, 68–70, 72, 153, 154
See application file for complete search history.

(56) References Cited

U.S. PATENT DOCUMENTS

| | | | |
|---|---|---|---|
| 5,482,732 A | 1/1996 | Kramer | |
| 5,685,717 A | 11/1997 | Kramer | |
| 6,554,615 B1 | 4/2003 | Brodkin | |
| 2003/0073563 A1 | 4/2003 | Brodkin | |
| 2004/0232576 A1* | 11/2004 | Brodkin | A61K 6/17 264/16 |
| 2005/0064369 A1* | 3/2005 | Zel | A61K 6/822 433/203.1 |
| 2006/0099552 A1* | 5/2006 | van der Zel | A61C 13/081 433/223 |
| 2009/0215010 A1* | 8/2009 | Tagami | A61C 13/0024 433/223 |
| 2009/0298016 A1 | 12/2009 | Chu | |
| 2010/0133711 A1* | 6/2010 | Brodkin | A61C 5/70 264/19 |
| 2011/0275031 A1* | 11/2011 | Jana | A61C 13/0022 433/172 |
| 2012/0193823 A1* | 8/2012 | Goetzinger | B28B 7/28 264/16 |

FOREIGN PATENT DOCUMENTS

EP 1396237 A1 3/2004

OTHER PUBLICATIONS

International Search Report; PCT/US2017/055917; Jan. 10, 2018 (completed); dated Jan. 18, 2018.
Written Opinion of the International Searching Authority; PCT/US2017/055917; Jan. 10, 2018 (completed); dated Jan. 18, 2018.
International Preliminary Report on Patentability; PCT/US2017/055917; Jan. 10, 2018 (completed); dated Jan. 18, 2018.

* cited by examiner

*Primary Examiner* — Maria V Ewald
*Assistant Examiner* — Ethan A. Utt
(74) *Attorney, Agent, or Firm* — Dentsply Sirona Inc.

(57) ABSTRACT

The invention is related to a shaded porcelain system that contains two types of veneering porcelains: natural enamel/dentin body and opal enamel, as well as stain & glaze porcelain, with CTE that are compatible to and which can be used for veneering a dental prosthesis made of 1) lithium disilicate-based glass-ceramic substructure that is formed by hot pressing or CAD/CAM machined process or 2) YTZP zirconia-based ceramic substructure that is formed by CAD/CAM machined process in order to improve overall esthetics of final prosthesis.

8 Claims, No Drawings

SHADE-COORDINATED, VENEERING PORCELAIN SYSTEM FOR DENTAL PROSTHESES

THE CROSS-REFERENCE TO RELATED APPLICATIONS

This patent application claims the benefit of and priority to U.S. Provisional Patent Application Ser. No. 62/406,190, filed on Oct. 10, 2016, which is herein incorporated by reference for all purposes.

FIELD OF THE INVENTION

The invention is related to a shaded porcelain system that contains two types of veneering porcelains: natural enamel/dentin body and opal enamel, as well as stain and glaze porcelain with their CTEs (Coefficient of Thermal Expansion) that match to and thus can be used for veneering dental prostheses made of 1) lithium disilicate-based glass-ceramic substructure that is formed by hot pressing or CAD/CAM machining process or 2) YTZP zirconia-based ceramic substructure that is formed by CAD/CAM machining process in order to further improve the esthetics of final restorations. Particularly, the veneering porcelain, in powder form, can be applied and built upon the lithium disilicate-based glass-ceramic or the YTZP zirconia-based ceramic substructure in the form of coping and/or framework to form dental prosthesis (i.e., crowns and/or bridges); and the stain & glaze porcelain, in either powder or paste form, can be applied directly over full-contour, monochromatic lithium disilicate-based glass-ceramic or YTZP zirconia-based ceramic or over veneered lithium disilicate-based glass-ceramic or YTZP zirconia-based ceramic dental prosthesis to complete their final surface finish.

In addition to its thermal compatibility to both lithium disilicate-based glass-ceramic and YTZP zirconia-based ceramic substructure, the veneering porcelain has also been shaded according to the principle of a patented color correlation scheme (U.S. Pat. No. 5,482,732, U.S. Pat. No. 5,685,717) as such that when the veneering porcelain is applied and/or built upon lithium disilicate-based glass-ceramic versus YTZP zirconia-based ceramic substructure which have different degrees of translucency, have good shade coordination (i.e., value, chroma, hue, and translucency) between the two types of dental prosthesis.

BACKGROUND OF THE INVENTION

With increasing demand for more esthetic dental prosthesis and the adoption of the CAD/CAM technique to reduce labor-intensive lab work, the traditional method for making dental prosthesis, namely the hand-layered, step by step, porcelain-fused-to-metal (PFM) technique has been continuously in decline in recent years. Two important high-strength ceramic substructure materials in this category that are replacing metal framework are the lithium disilicate-based glass-ceramic and YTZP zirconia-based ceramic.

Owing to the closeness of CTEs between the high-strength lithium disilicate-based glass-ceramic and YTZP zirconia-based ceramic, the development of a common porcelain system that is compatible to both types of substructure is possible. To date, various brands of either ceramic substructure material are readily available in the market that also offer shaded veneering porcelain and stain porcelain to improve esthetics as well as glaze porcelain to provide a gloss surface finish of dental restorations.

However, due to the use of different types of material for the substructure, shade consistency of final dental prosthesis made between these two types of substructure materials and veneered with the one common shade of the veneering porcelain available in the market remains a challenge. Hence, a better shade coordinated porcelain system for veneering over both high-strength lithium disilicate-based glass-ceramic and YTZP zirconia-based ceramic is necessary.

SUMMARY OF THE INVENTION

It is one object of the present invention to provide a veneering porcelain system with its CTE that is compatible to both high-strength lithium disilicate-based glass-ceramic and YTZP zirconia-based ceramic. CTE of the veneering porcelain is in the range of 9.0 ppm/° C. and 9.5 ppm/° C. @ 500° C.; CTE of the lithium disilicate-based glass-ceramic is in the range of 9.5 ppm/° C. and 10.5 ppm/° C. @ 500° C.; and CTE of the YTZP zirconia-based ceramic is in the range of 10.0 ppm/° C. and 10.5 ppm/° C.

The invention is further related to a dental porcelain system that contains the following two types of veneering porcelain: natural enamel/dentin body and opal enamel, as well as glaze and stain porcelain. The natural enamel/dentin body porcelain provides either as enamel without opalescence for incisal portion or a dentin body of a dental prosthesis and the opal enamel provides an incisal layer that radiate opalescence to simulate natural dentition. The stain porcelain, when applied over full-contour lithium disilicate-based glass-ceramic or YTZP zirconia-based ceramic, is to provide relevant shade to the dental prosthesis whereas the glaze porcelain provides the gloss surface finish of dental prosthesis.

It is another object of the present invention to design/formulate a shade coordinated porcelain system using the patented color correlation scheme (U.S. Pat. No. 5,482,732, U.S. Pat. No. 5,685,717), when veneered/applied over high-strength lithium disilicate-based glass-ceramic versus YTZP zirconia-based substructure, to provide a shade consistency between the two types of dental prosthesis.

It is another object of the present invention a shade-coordinated porcelain system is provided comprising natural enamel/dentin body, opal enamel, as well as stain & glaze porcelain that is thermally compatible to each other as well as to both lithium disilicate-based glass-ceramic and YTZP zirconia-based ceramic substructure for making dental prosthesis; wherein CTE of the said porcelains in the shade-coordinated porcelain system is in the range between 8.8 ppm/° C. and 9.5 ppm/° C. @ 500° C., in order to be compatible to the said lithium disilicate-based glass-ceramic with CTE in the range of 9.5 ppm/° C. and 10.5 ppm/° C. @ 500° C.; and the said YTZP zirconia-based ceramic with CTE in the range of 10.0-11.0 ppm/° C. @ 500° C.

It is another object of the present invention, firing temperature of the said veneering porcelain preferably may be in the range between 680° C. and 840° C., more preferably in the range between 720° C. and 800° C., and most preferably in the range between 740° C. and 780° C. Firing temperature of the said stain & glaze porcelain is preferably 50° C., more preferably 30° C., and most preferably 10° C.-20° C. lower than the firing temperature of natural enamel/dentin body and opal enamel porcelain.

It is another object of the present invention, shade development of the veneering porcelain according to the principle of a patented color correlation scheme may be as such that when the veneering porcelain is applied and/or built upon lithium disilicate-based glass-ceramic versus YTZP zirconia-based ceramic substructure which have different degrees of translucency, have good shade coordination (i.e., value, chroma, hue, & translucency) between the two types of prosthesis.

It is another object of the present invention, that CTEs of the said veneering porcelain and stain & glaze porcelain are in the range between 9.0 ppm/° C. and 9.5 ppm/° C. @ 500° C. and said porcelain firing temperatures are in the range between 750° C. and 770° C.

It is another object of the present invention that shade development of the veneering porcelain according to the principle of a patented color correlation scheme (U.S. Pat. No. 5,482,732, U.S. Pat. No. 5,685,717) may be as such that when the veneering porcelain is applied and/or built upon lithium disilicate-based glass-ceramic versus YTZP zirconia-based ceramic substructure which have different degrees of translucency, have good shade coordination (i.e., value, chroma, hue, & translucency) between the two types of prosthesis.

DESCRIPTION OF THE PREFERRED EMBODIMENTS

The present invention provides for a shade-coordinated, veneering porcelain system for a dental prosthesis. Generally, the shade-coordinated, veneering porcelain system for a dental prosthesis may be made of hot-pressed or CAD/CAM machined lithium silicate-based material (e.g., lithium disilicate and/or monosilicate, preferably lithium disilicate) or CAD/CAM machined YTZP zirconia-based material. More particularly, the invention comprises a shade coordinated porcelain system, which contains two, type of veneering porcelain: natural enamel/dentin body and opal enamel porcelain, as well as glaze and stain porcelain, that are thermally compatible with both lithium disilicate-based glass-ceramic and YTZP zirconia-based ceramic substructure. With its well-designed shade scheme, shade coordination can be obtained between these two types of dental prosthesis.

The composition of the natural enamel/body white porcelain in powder form (see Table 1) is formulated such that after first dentin porcelain firing, it is refractory and is resistant to drifting during subsequent second dentin or enamel porcelain firing for making either lithium disilicate-based glass-ceramic or YTZP zirconia-based ceramic restorations. In addition, it is also thermally compatible with the above two types of glass ceramic/ceramic. The firing temperature of the natural enamel/dentin body porcelain in powder form is preferably between 680° C. and 840° C., more preferably between 720° C. and 800° C., and most preferably between 740° C. and 780° C.

TABLE 1

CHEMICAL COMPOSITION OF NATURAL ENAMEL/BODY WHITE PORCELAIN (WT %)

| Oxide | Natural Enamel/Body White |
|---|---|
| $SiO_2$ | 55-70 (60-65) |
| $Al_2O_3$ | 5-18 (10-13) |
| $Na_2O$ | 0.5-13 (5-7) |
| $K_2O$ | 1-14 (6-9) |
| $Li_2O$ | 0.05-8 (1-3) |
| CaO | 0-7 (0-2) (0.05-1) |
| BaO | 0.5-9 (2-4) |
| MgO | 0-3 (0.5-1) (0.005-0.05) |

TABLE 1-continued

CHEMICAL COMPOSITION OF NATURAL ENAMEL/BODY WHITE PORCELAIN (WT %)

| Oxide | Natural Enamel/Body White |
|---|---|
| $CeO_2$ | 0-3 (0.5-1) (0.05-1) |
| $Sb_2O_3$ | 0-3 (0.5-1) (0.05-1) |
| $Tb_2O_3$ | 0-3 (0.5-1) (0.05-1) |
| $TiO_2$ | 0.14 (0-1) |
| $SnO_2$ | — |
| $B_2O_3$ | 0.5-10 (3-5) |
| $ZrO_2$ | 0-3 (0.5-1) (0.05-1) |
| $P_2O_5$ | 0-3 (0.5-1) |
| F | 0-3 (0.5-1) (0.05-1) |
| Total | 100 |

The composition of the opal enamel porcelain (see Table 2) is formulated such that it is thermally compatible with the above the two types of glass ceramic/ceramic as well as natural enamel/dentin body porcelain. The firing temperature of the opal enamel porcelain is preferably between 680° C. and 840° C., more preferably between 720° C. and 800° C., and most preferably between 740° C. and 780° C.

TABLE 2

CHEMICAL COMPOSITION OF OPAL ENAMEL WHITE PORCELAIN (WT %)

| Oxide | Opal Enamel White (Range) |
|---|---|
| $SiO_2$ | 53-68 (58-63) |
| $Al_2O_3$ | 5-18 (10-13) |
| $Na_2O$ | 0.5-13 (5-8) |
| $K_2O$ | 1-14 (6-9) |
| $Li_2O$ | 0.05-8 (1-3) |
| CaO | 0.05-8 (1-3) |
| BaO | 0.05-8 (1-3) |
| MgO | 0-2 (0.05-1) |
| $CeO_2$ | 0-2 (0.05-1) |
| $Sb_2O_3$ | 0-2 (0.05-1) |
| $Tb_2O_3$ | 0-5 (0.05-2) |
| $TiO_2$ | 0.14 (0-1) |
| $SnO_2$ | 0-2 (0.05-1) |
| $B_2O_3$ | 1-11 (3-6) |
| $ZrO_2$ | 0-2 (0.05-1) |
| $P_2O_5$ | 0-2 (0.05-1) |
| F | 0-2 (0.05-1) |
| Total | 100 |

Furthermore, the present invention may include an add-on (e.g. correction porcelain, formulation resulting in the composition in Table 3. The firing temperature of the add-on porcelain is preferably similar to that of the Natural Enamel/Body White composition, the Opal composition as described above.

TABLE 3

CHEMICAL COMPOSITION OF ADD-ON ENAMEL (WT %)

| Oxide | Add-On Enamel (Range) |
|---|---|
| $SiO_2$ | 51-71 (56-66) |
| $Al_2O_3$ | 1-20 (15-25) |
| $Na_2O$ | 1-20 (2-15) |
| $K_2O$ | 1-20 (2-12) |
| $Li_2O$ | 0.05-8 (1-4) |

TABLE 3-continued

| CHEMICAL COMPOSITION OF ADD-ON ENAMEL (WT %) | |
| --- | --- |
| Oxide | Add-On Enamel (Range) |
| CaO | 0.05-8 (1-4) |
| BaO | 0.5-10 (1-6) |
| MgO | 0-2 (0.05-1) |
| $CeO_2$ | 0-2 (0.05-1) |
| $Sb_2O_3$ | 0-2 (0.05-1) |
| $Tb_2O_3$ | 0-5 (0.5-4) |
| $TiO_2$ | 0.14 (0-1) |
| $SnO_2$ | 0-2 (0.05-1) |
| $B_2O_3$ | 1-12 (3-9) |
| $ZrO_2$ | 0-2 (0.05-1) |
| $P_2O_5$ | 0-2 (0.05-1) |
| F | 0-2 (0.05-1) |
| Total | 100 |

It is appreciated that the Natural Enamel/Body White composition, the Opal composition and/or the add-on composition of TABLES 1-3 may be formed from the combination of at least two different granulated frit materials. Generally, a frit material may be a ceramic composition that has been fused in a heating apparatus (furnace, fusing oven, etc. . . . ), quenched to form a glass, and then granulated. Various exemplary chemical compositions of the granulated frit materials of the present invention are shown in TABLE 4A.

TABLE 4A

| CHEMICAL COMPOSITION OF FRITS (WT %) | | | | | | |
| --- | --- | --- | --- | --- | --- | --- |
| Oxide/wt % | Frit A | Frit B | Frit C | Frit D | Frit E | Frit F |
| $SiO_2$ | 62-68 | 62-66 | 58-62 | 66-70 | 63-67 | 57-61 |
| $Al_2O_3$ | 12-16 | 14-18 | 8-12 | 12-16 | 5-9 | 9-13 |
| $K_2O$ | 7-11 | 12-16 | 3-7 | 5-9 | 10-14 | 6-10 |
| $Na_2O$ | 3-7 | 2-6 | 4-8 | 5-9 | 8-12 | 8-12 |
| $Li_2O$ | 1-5 | 0.5-3 | 1-5 | 0.05-0.5 | 0.05-1 | 0.05-1 |
| CaO | 0.05-1 | 0.05-1 | 0.05-1 | 1-3 | 9.05-1 | 1-5 |
| BaO | 0.5-3 | | 2-6 | 0.05-1 | 1.98 | |
| MgO | | 0.05-1 | | | | |
| $CeO_2$ | 0.5-3 | 0.05-1 | 0.05-1 | | | 0.5-1 |
| $Sb_2O_3$ | 0.005-1 | | 0.01-0.5 | 1-3 | 2.25 | |
| $Tb_2O_3$ | | 0.05-1 | 1-4 | | | 1-4 |
| $TiO_2$ | | | 0.05-1 | | | |
| $SnO_2$ | | | | | | 0.5-3 |
| $B_2O_3$ | | | 8-12 | | | 2-6 |
| $ZrO_2$ | 1-3 | | | | | |
| $P_2O_5$ | | | | | | 0.5-4 |
| $F^-$ | | | | 0.5-1 | 0.5-3 | |
| Total | 100.0 | 100.0 | 100.0 | 100.00 | 100.00 | 100.00 |

Preferably, the Natural Enamel/Body White composition, the Opal composition and/or the add-on composition of TABLES 1-3 may be formed from the combination of at least three different granulated frit materials and most preferably at least four different granulated frit materials (e.g., from three to six different granulated frit materials) as shown in TABLE 4B.

TABLE 4B

CHEMICAL COMPOSITION OF RESULTANT PORCELAINS (WT %)

| Component frits | Natural Enamel/ Body White Wt % | Opal Wt % | Add-on Wt % |
|---|---|---|---|
| Frit A | 20-40 (25-35) | 0-60 (30-50) | 0-60 (30-50) |
| Frit C | 25-45 (30-40) | 20-40 (25-35) | 45-65 (50-60) |
| Frit D | 5-25 (10-20) | 15-35 (20-30) | 1-20 (5-15) |
| Frit B | 0-5 (1-3) | 0-5 (1-3) | 0-4 (0.05-2) |
| Frit E | 10-30 (15-25) | 0-30 (10-20) | 1-15 (2-8) |
| Frit F | 0-60 (30-50) | 30-50 (35-45) | 15-35 (20-30) |

The composition of the glaze and stain white porcelain (see Table 5) is formulated such that it can be applied and fired either directly over either full-contour or veneered lithium disilicate-based glass-ceramic and YTZP zirconia-based ceramic substructure to form dental restorations at a lower temperature than both natural enamel/dentin body and opal enamel porcelain. The firing temperature of the stain and glaze porcelain is preferably 50° C., more preferably 30° C., and most preferably 10-20° C. lower than the firing temperature of natural enamel/dentin body and opal enamel porcelain.

TABLE 5

CHEMICAL COMPOSITION OF GLAZE & STAIN PORCELAIN (WT %)

| Oxide | Glaze & Stain White |
|---|---|
| $SiO_2$ | 53-68 (58-63) |
| $Al_2O_3$ | 5-18 (10-13) |
| $Na_2O$ | 0.5-13 (5-8) |
| $K_2O$ | 1-14 (4-10), (6-9) |
| $Li_2O$ | 0.05-8 (1-3) |
| CaO | 0.05-2 (1-3) |
| BaO | 0.05-9 (2-6), (1-3) |
| $CeO_2$ | 0-2 (0.05-1) |
| $Sb_2O_3$ | 0-2 (0.005-1) |
| $Tb_2O_3$ | 0.5-5 (0-2) |
| $TiO_2$ | 0.42 (0-1) |
| $B_2O_3$ | 1-15 (5-12), (3-6) |
| Total | 100 |

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled.

The disclosures of all articles and references, including patent applications and publications, are incorporated by reference for all purposes.

REFERENCE

U.S. Pat. No. 5,482,732 "Dental Porcelain Shading Method" by Carolyn Kramer Jun. 9, 1994.

U.S. Pat. No. 5,685,717 "Dental Porcelain Shading Kit, System and Method" by Carolyn Kramer May 31, 1995.

The invention claimed is:

1. A shade-coordinated porcelain system for a lithium disilicate-based glass-ceramic and/or YTZP zirconia-based ceramic substructure, comprising:

(i) a natural enamel/dentin body having a composition that includes:

| Oxide | Natural Enamel/ Body White (wt %) |
|---|---|
| $SiO_2$ | 60-65 |
| $Al_2O_3$ | 10-13 |
| $Na_2O$ | 5-7 |
| $K_2O$ | 6-9 |
| $Li_2O$ | 1-3 |
| CaO | 0-2 |
| BaO | 2-4 |
| MgO | 0.5-1 |
| $CeO_2$ | 0.5-1 |
| $Sb_2O_3$ | 0.5-1 |
| $Tb_2O_3$ | 0.5-1 |
| $TiO_2$ | 0-1 |
| $SnO_2$ | 0 |
| $B_2O_3$ | 3-5 |
| $ZrO_2$ | 0.5-1 |
| $P_2O_5$ | 0.5-1 |
| F | 0.5-1 |
| Total | 100 |

(ii) an opal enamel having a composition that includes:

| Oxide | Opal Enamel (wt %) |
|---|---|
| $SiO_2$ | 58-63 |
| $Al_2O_3$ | 10-13 |
| $Na_2O$ | 5-8 |
| $K_2O$ | 6-9 |
| $Li_2O$ | 1-3 |
| CaO | 1-3 |
| BaO | 1-3 |
| MgO | 0.05-1 |
| $CeO_2$ | 0.05-1 |
| $Sb_2O_3$ | 0.05-1 |
| $Tb_2O_3$ | 0.05-2 |
| $TiO_2$ | 0-1 |
| $SnO_2$ | 0.05-1 |
| $B_2O_3$ | 3-6 |
| $ZrO_2$ | 0.05-1 |
| $P_2O_5$ | 0.05-1 |
| F | 0.05-1 |
| Total | 100 | and (iii) a stain and/or glaze porcelain having a composition that includes:

| Oxide | Stain and/or Glaze (wt %) |
|---|---|
| $SiO_2$ | 58-63 |
| $Al_2O_3$ | 10-13 |
| $Na_2O$ | 5-8 |
| $K_2O$ | 4-10 |
| $Li_2O$ | 1-3 |
| CaO | 1-3 |
| BaO | 2-6 |
| $CeO_2$ | 0.05-1 |
| $Sb_2O_3$ | 0.005-1 |
| $Tb_2O_3$ | 0-2 |
| $TiO_2$ | 0-1 |
| $B_2O_3$ | 5-12 |
| Total | 100 | wherein the natural enamel/dentin body, the opal enamel, and the stain and/or glaze porcelain are thermally compatible to the substructure and have a CTE in the range between 8.8 ppm/° C. and 9.5 ppm/° C. @ 500° C. and wherein the CTE of the natural enamel/dentin body and the opal enamel is achieved after firing the shade-coordinated porcelain system at a temperature in the range between 680° C. and 800° C.

2. The shade-coordinated porcelain system of claim 1, wherein the lithium disilicate-based glass-ceramic substructure has a CTE in the range of 9.5 ppm/° C. and 10.5 ppm/° C. @ 500° C.

3. The shade-coordinated porcelain system of claim 1, wherein the YTZP zirconia-based ceramic substructure has a CTE in the range of 10.0-11.0 ppm/° C. @ 500° C.

4. The shade-coordinated porcelain system of claim 1, wherein the CTE of the natural enamel/dentin body, the opal enamel, and the stain and/or glaze porcelain is achieved after firing the shade-coordinated porcelain system at a temperature in the range between 720° C. and 800° C.

5. The shade-coordinated porcelain system of claim 4, wherein the CTE is achieved after the firing the shade-coordinated porcelain system at a temperature 50° C. lower than the firing temperature of natural enamel/dentin body.

6. The shade-coordinated porcelain system of claim 4, wherein the CTE is achieved after firing the shade-coordinated porcelain system at a temperature 50° C. lower than the firing temperature of the opal enamel porcelain.

7. The shade-coordinated porcelain system of claim 4, wherein the CTEs of the natural enamel/dentin body or the opal enamel porcelain and stain and/or glaze porcelain are in the range between 9.0 ppm/° C. and 9.5 ppm/° C. @ 500° C. and the porcelain firing temperatures are in the range between 750° C. and 770° C.

8. The shade-coordinated porcelain system of claim 1, wherein the CTE of the natural enamel/dentin body, the opal enamel, and the stain and/or glaze porcelain is achieved after firing the shade-coordinated porcelain system at a temperature in the range between 740° C. and 780° C.

* * * * *